United States Patent [19]

Diamond

[11] B 4,001,231

[45] Jan. 4, 1977

[54] PROCESS FOR MAKING A METHENAMINE SALT OF AN OPTICALLY ACTIVE ACID

[75] Inventor: Julius Diamond, Morris Plains, N.J.

[73] Assignee: William H. Rorer, Inc., Fort Washington, Pa.

[22] Filed: Mar. 29, 1973

[21] Appl. No.: 332,442

[44] Published under the second Trial Voluntary Protest Program on March 30, 1976 as document No. B 332,442.

[52] U.S. Cl. .............................. 260/248.5; 424/249
[51] Int. Cl.² ..................................... C07D 251/04
[58] Field of Search ................................ 260/248.5

[56] References Cited

UNITED STATES PATENTS

| 569,429 | 10/1896 | Schiff | 260/248.5 |
| 2,539,483 | 1/1951 | Ruskin | 260/248.5 X |
| 3,168,452 | 2/1965 | Debe | 260/248.5 X |
| 3,372,091 | 3/1968 | Harnett et al. | 260/248.5 X |
| 3,597,428 | 8/1971 | Hechenbliekner | 260/248.5 |

*Primary Examiner*—John M. Ford
*Attorney, Agent, or Firm*—James A. Nicholson

[57] ABSTRACT

Novel salts of hexamethylenetetramine formed from d- or l- enantiamorph of a selected acid are disclosed, and a process for the preparation is described. A new method for the treatment of urinary tract infections is also described.

1 Claim, No Drawings

PROCESS FOR MAKING A METHENAMINE SALT OF AN OPTICALLY ACTIVE ACID

This invention describes new salts of hexamethylenetetramine and particularly to salts formed with either the d- or the l- enantiamorph of a selected acid. Hexamethylenetetramine is commonly known as methenamine. This invention also described a new method for the treatment of urinary tract infections by the administration of novel methenamine compounds.

Methenamine has been used for about seventy-five years as a urinary antiseptic and it has received this universal, long-term acceptance because it is effective while being relatively nontoxic. Methenamine per se is not active as a drug, but in the presence of an acid urine, it hydrolyzes and liberates formaldehyde. This formaldehyde is effective against bacteria, fungi, and virus and the exceptional utility of methenamine lies in the fact that it produces formaldehyde at the site of infection.

Another feature of methenamine is that it possesses the convenience of being taken orally. It is absorbed as methenamine from the intestinal tract into the blood stream, it circulates unchanged in all body fluids, and is rapidly excreted in the urine. Because, as mentioned above, methenamine is attacked by an acid environment, it has been deduced that from 10 to 30% of it is destroyed by gastric juice, but this can be compensated for by the administration of a compensating dose. Of, the methenamine can be enteric coated so that it passes unchanged into the intestine without being attacked by stomach acids.

Methenamide has particular value in the prophylactic and therapeutic treatment of cystitis due to bacterial invasion of the bladder itself or due to infection of the kidney (pyelonephritis), prostate, or urethra. Cystitis usually is symptomatically evidenced by frequent and burning urination and the presence of pus in the voided urine. Such urinary tract infections are frequently treated with antibiotics and sulfa drugs but because of their somewhat specific activities, they may require a urine culture to selectively choose the best one. In addition, those more potent drugs are coupled with an increased toxicity and this may rule against their prolonged use. On the other hand, methenamine has a broad spectrum of activity and its continued administration over a period of many months indicates the versatility of its use.

Although methenamine has the advantages of wide spectrum bacteriacidal activity and low toxicity, it has the disadvantage of requiring a constant acidic urine to induce the continuous yield of formaldehyde. To achieve this the urine should be maintained at pH 5.0 or lower and this has generally been accomplished by the concomitant oral adminstration of a urine acidifying agent such as ascorbic acid, sodium acid phosphate, ammonium chloride, methionine and the like. This separate administration of the acidifying agent has called for frequent pH assay of the urine and a constant reminder to the patient to take the second, acidifying agent. The result has been a rather haphazard coadministration of the acidifying agent along with the methenamine.

The problem of maintaining an acid urine environment is accentuated by the fact that when methenamine is hydrolyzed, it yields not only formaldehyde, but it also yields ammonia. In fact, one molecule of methenamine produces four molecules of ammonia. This large amount of ammonia in the urine serves to diminish or arrest further hydrolysis of the methenamine due to the alkaline property of ammonia. It is apparent, therefore, that even in an initially acid urine, as the methenamine decomposes to form formaldehyde and ammonia, the ammonia serves as a counteracting agent to defeat the further hydrolysis of methenamine.

In an effort to assure the conjoint administration of methenamine and an acidifying agent, acid salts of methenamine are being commercially supplied. The salts of methenamine, heretofore known, have been formed with the racemic mixture of acids having an asymmetrical carbon atom, or have been formed by the addition of acids having symmetrical carbon atoms. An illustration of the former is U.S. Pat. No. 3,004,026 which issued to Alexander Galat on Oct. 10, 1961, and an illustration of the latter is U.S. Pat. No. 2,764,581 which issued to Heinrich Scholz et al. on Sept. 25, 1956. U.S. Pat. No. 3,004,026 discloses the preparation of hexamethylenetetramine alinate, but there is no mention of either the d- or the l- form of the acid and therefore it must contemplate only the use of the racemic mixture, that is, hexamethylenetetramine d,l-alinate. The acids mentioned in U.S. Pat. No. 2,764,581 do not have optically active forms. Another patent of interest U.S. Pat. No. 3,007,438 to T. I. Fand, et al., of Feb. 12, 1963, which refers to methenamine mandelate, that is methenamide d,l-mandelate.

The compounds of these patents are representative of salts of methenamine which are taken orally because of their urinary antiseptic value. For instance, U.S. Pat. No. 3,004,026 points out that the methenamine moiety of the salt yields ammonia and the germicidal agent formaldehyde in an acid urine. The patent also explains theat the alinine acid moiety of the salt, d,l-alinine acid, produces or contributes to the acidity of the urine which is necessary to hydrolyze the methenamine so that formaldehyde is released in the urine. The acidity of the released d,l-alinine acid also serves to neutralize the ammonia which is an unavoidable by-product of the hydrolyzed methenamine.

U.S. Pat. No. 3,004,026 also states that when methenamine, in its base form, is administered to a person, it has been a common practice to conjointly administer a salt which exhibits an acid reaction, such as ammonium chloride. Another common practice has been to separately but simultaneously administer with the methenamine base an acid such as mandelic acid or aninine acid. Other acids which have been conjointly administered are ascorbic acid and methionine.

In all instances, there has been no suggestion that either the d- of the l- form of these acids should selectively be used. Further, these salts of methenamine supply the acid only in a 1 to 1 ratio relative to the methenamine and this is far below the 4 to 1 ratio which is necessary as has been explained.

The feature of the present invention is the chemical formation of salts of methenamine which are formed solely with either d- or with the l- form of acids having these optically active forms. The acids which are useful for this purpose are alinine, mandelic, ascorbic and 2-amino-4-methylthiobutanoic (methionine) acids. The d- or l- forms of these acids are commercially available or can be obtained by known resolution procedures.

The utility of these d- and l- acid salts of methenamine resides in the unexpected discovery that the peak appearance of methenamine in the urine occurs about 6 hours after oral administration. It has also been unexpectedly discovered that when the racemic acid is orally administered, the optical isomers are excreted at different times. One example of such action is mandelic acid where it has been found that l- mandelic acid is excreted in the urine prior to the excretion of d- mandelic acid. It has further been found that l- mandelic acid appears in peak concentration in the urine about 2 hours after oral administration of the racemic acid mixture whereas d- mandelic acid appears in peak concentration in the urine about 6 hours after this administration.

I have found that administration of the d- mandelic acid salt of methenamine results in the approximately simultaneous appearance in the excreted urine of both methenamine and d- mandelic acid. This means that there is acid present to hydrolyze the methenamine at the time that this is required to evolve the formaldehyde. Thus, administration of this novel methenamine d- mandelic acid to persons having a urinary infection results in the most favorable urine sterilizing conditions by supplying the needed urine acid in a more favorable ratio with methenamine. Other d- or l- forms of optically active acids may also be used depending upon the desired acidity of the urine at a specific time. Such d- or l- acids which may be used for this purpose will of course be one which exhibits the property of appearing in the urine about 4–8 hours after oral administration. Such acids, for example, are the d- or l- form of alinine acid, ascorbic acid, 2-amino-4-methylthiobutanoic acid and the like.

Although the d- mandelic acid salt of methenamine has been described above in particular, it is to be understood that the l- mandelic acid salt of methenamine and d- and l- forms of the named acid salts of methenamine are included in the present invention as they are also of particular value. The l- mandelic acid salt of methenamine can be administered with therapeutic advantage because of the reservoir action of the bladder. Thus, even though the l- acid component of the salt appears in the urine about two hours after the salt has been administered, it is present in the bladder to bring about the hydrolysis of the methenamine when it is excreted therein about 4 hours later. Although this is of lesser value, from a therapeutic viewpoint, the fact remains that the l- acid salt of methenamine is useful particularly if a person is taking this salt at repeated intervals throughout the day. The overlapping of the excretion of methenamine and the l- acid, from the kidneys, results in a general overall contact of the l- acid with the methenamine to cause the latter to release formaldehyde. This effect is also of value with other d- or l- forms of the other salts mentioned above depending once again on the effect desired.

The recommended daily effective dose of methenamine is 4 to 5 grams (but it may be as high as 8 grams) daily. The compounds of this invention may be administered in doses that will provide the effective amount of methenamine daily. Since the methenamine administered will eventually become effective, amounts as low as one-fourth the amount normally administered will provide the same effectiveness. This will produce a more uniform concentration of formaldehyde in the urine.

The process for making either the d- acid salt of the l- acid salt is the same, as it depends on the selection of the desired d- or l- form. The selected one is combined with the methenamine in a molar ratio of 0.8:1.0 to 1.0:0.8, but preferably in a 1:1 ratio, in a common solvent such as methyl ethyl ketone, the mixture being at an elevated temperature. The methenamine salt of the acid is formed as crystals which can then be recovered by decanting or filtering, after which the crystals are washed with the solvent and then dried.

The d- or l- acid salt of methenamine will be formed in low yields if the aforementioned generalized procedure is carried out, but optimum yields are obtained if a hot solution of the d- or l- acid form in methyl ethyl ketone is slowly added to a boiling suspension of methenamine in the same ketone. Instead of this ketone, other common solvents may be used, such as acetone, ethanol, and isopropanol. During the addition of the acid, vigorous stirring should be carried on and when the addition is completed, the heat source is removed. While the reaction mixture is cooling to room temperature, it is best that its stirring be continued but it may be at a slower rate. It is then cooled in an ice-water bath to induce increased crystallization of the salt.

The recovered salt may be formulated in capsules or in tablets for oral use. The salt is not subject to deterioration and the pharmaceutical preparation will stand ordinary shelf life. Enough of the salt would be taken, preferably at spaced intervals, so that the total daily consumption of the methenamine content is from 1 to 8 grams.

The scope of this invention claims these novel methenamine salt compounds per se, the processes for preparing the same, and their use in the treatment of urinary tract infections.

Representative examples of the invention are the following:

EXAMPLE 1

Methenamine dextro-mandelate

To a boiling suspension of 140 ml. of methyl ethyl ketone containing 18.7 g. (0.133 mole) of methenamine is slowly added a hot solution of 20.3 g (0.133 mole) of d-mandelic acid in 50 ml. of methyl ethyl ketone with vigorously stirring. The heat source is removed. The reaction mixture is stirred to room temperature, and then cooled in an ice-water bath. White crystals are collected by filtration, washed with a small amount of methyl ethyl ketone, followed by anhydrous ether, and dried at 50° C. in vacuum for 3 hours to obtain methenamine dextro-mandelate. mp. 133–4° C $[c]_D^{21} + 62.0°$ (C = 3,H$_2$O)

EXAMPLE 2

Methenamine levo-mandelate

To a boiling suspension of 160 ml. of methyl ethyl ketone containing 23.0 g. (0.165 mole) of methenamine is slowly added a hot suspension of 25 g. (0.16 mole) of l-mandelate acid in 60 ml. of methyl ethyl ketone. The heat source is removed. The solution is stirred to room temperature, then cooled in an ice-water bath. White crystals are collected by filtration, washed with a small amount of cold methyl ethyl ketone, followed by anhydrous ether, and dried at 50° C. in vacuum for 4.5 hours to obtain methenamine levo-mandelate. mp. 133.5°–135.5° C $[\alpha]_D^{20} -63.3°$ (C = 3,H$_2$O)

EXAMPLE 3

In either Examples 1 or 2, the ketone may be replaced with another solvent such as acetone, ethanol or isopropanol.

EXAMPLE 4

In either of the Examples 1 or 2, the amount of acid may be increased or decreased by about 20%.

EXAMPLE 5

In Example 1, the d-mandelic acid may be replaced by 23.8 g. of d-alinine acid, 23.4 g. of d-ascorbic acid or 19.7 g. of d-methionine to obtain methenamine dextro-alinate, methenamine dextro-ascorbate or the dextro-methionine salt of methenamine.

EXAMPLE 6

In Example 2, the l-mandelic acid may be replaced by 29.5 g. of l-alinine acid, 29.0 g. of l-ascorbic acid or 24.6 g. of l-methionine to obtain methenamine levo-alinate, methenamine levo-ascorbate or the levo-metionine salt of methenamine.

EXAMPLE 7

The variations of Examples 3 and 4 are applied to Examples 5 and 6.

I claim:

1. The process for making a salt of methenamine which comprises slowly adding d-mandelic acid to a boiling, stirred suspension of methenamine in a solvent selected from the group consisting of ethyl methyl ketone, acetone, ethanol and isopropanol, in the molar ratio of 0.8:1.0 to 1.0:0.8, removing the heat but continuing the stirring until the mixture cools to room temperature, cooling in an ice-water bath and recovering the formed crystals of methenamine dextro-mandelate.

* * * * *